US006999163B2

(12) United States Patent
Pike

(10) Patent No.: US 6,999,163 B2
(45) Date of Patent: Feb. 14, 2006

(54) EMBEDDED MOEMS SENSOR FOR FLUID DIELECTRICS IN RF APPLICATIONS

(75) Inventor: Randy T. Pike, Grant, FL (US)

(73) Assignee: Harris Corporation, Melbourne, FL (US)

( * ) Notice: Subject to any disclaimer, the term of this patent is extended or adjusted under 35 U.S.C. 154(b) by 354 days.

(21) Appl. No.: 10/628,846

(22) Filed: Jul. 28, 2003

(65) Prior Publication Data
US 2005/0024629 A1 Feb. 3, 2005

(51) Int. Cl.
G01N 21/41 (2006.01)
(52) U.S. Cl. ..................................... 356/128
(58) Field of Classification Search ......... 356/128–137
See application file for complete search history.

(56) References Cited

U.S. PATENT DOCUMENTS

| 4,102,574 | A | * | 7/1978 | Wieder et al. ............... 356/367 |
|---|---|---|---|---|
| 4,555,930 | A | | 12/1985 | Leach et al. |
| 5,099,121 | A | | 3/1992 | Allen |
| 5,162,972 | A | | 11/1992 | Gripshover et al. |
| 5,208,465 | A | | 5/1993 | Jacobson |
| 5,822,073 | A | | 10/1998 | Yee et al. |
| 5,962,589 | A | | 10/1999 | Matsumoto et al. |
| 5,991,048 | A | | 11/1999 | Karlson et al. |
| 6,233,532 | B1 | | 5/2001 | Boudreau et al. |
| 6,268,125 | B1 | | 7/2001 | Perkins |
| 6,286,493 | B1 | | 9/2001 | Aoki |
| 6,341,599 | B1 | | 1/2002 | Hada et al. |
| 6,478,940 | B1 | | 11/2002 | Suzuki et al. |
| 6,497,808 | B1 | | 12/2002 | Yamauchi et al. |
| 6,515,235 | B1 | | 2/2003 | Moller |
| 6,806,416 | B1 | | 10/2004 | Pike |
| 6,870,439 | B1 | | 3/2005 | Brown et al. |
| 6,873,229 | B1 | | 3/2005 | Pike |
| 6,873,305 | B1 | | 3/2005 | Rawnick et al. |
| 6,876,274 | B1 | | 4/2005 | Brown et al. |
| 6,876,278 | B1 | | 4/2005 | Rawnick et al. |
| 6,879,297 | B1 | | 4/2005 | Brown et al. |
| 6,888,422 | B1 | | 5/2005 | Rawnick et al. |
| 6,888,500 | B1 | | 5/2005 | Brown et al. |
| 6,891,501 | B1 | | 5/2005 | Rawnick et al. |
| 6,894,583 | B1 | | 5/2005 | Brown et al. |
| 6,894,591 | B1 | | 5/2005 | Rawnick et al. |
| 6,894,652 | B1 | | 5/2005 | Rawnick et al. |
| 6,906,668 | B1 | | 6/2005 | Rawnick et al. |
| 6,909,404 | B1 | | 6/2005 | Rawnick et al. |
| 6,914,575 | B1 | | 7/2005 | Rawnick et al. |
| 6,930,568 | B1 | | 8/2005 | Snyder et al. |
| 6,930,572 | B1 | | 8/2005 | Rawnick et al. |
| 6,930,653 | B1 | | 8/2005 | Rawnick et al. |

(Continued)

Primary Examiner—Gregory J. Toatley, Jr.
Assistant Examiner—Amanda Merlino
(74) Attorney, Agent, or Firm—Sacco & Associates, PA

(57) ABSTRACT

An RF system (100) can include one or more RF circuits (108) coupled to a fluid dielectric (106). The RF circuit can be disposed on a portion of a dielectric substrate (102) which also contains the fluid dielectric. A light source 302 is provided for transmitting optical radiation through a portion of the fluid dielectric in a transmitted direction. A sensor (304) measures at least one parameter indicative of a change of direction of the optical radiation relative to the transmitted direction. According to one aspect, the light source and/or the sensor can be disposed within the dielectric substrate of the RF system. An output of the sensor can be coupled to a processor (322, 422) for determining a condition of the fluid dielectric based on the measured parameter.

28 Claims, 3 Drawing Sheets

U.S. PATENT DOCUMENTS

| | | |
|---|---|---|
| 2004/0155727 A1 | 8/2004 | Snyder et al. |
| 2004/0178865 A1 | 9/2004 | Rawnick et al. |
| 2004/0207481 A1 | 10/2004 | Brown et al. |
| 2004/0207494 A1 | 10/2004 | Brown et al. |
| 2004/0227687 A1 | 11/2004 | Delgado et al. |
| 2004/0239577 A1 | 12/2004 | Delgado et al. |
| 2004/0252069 A1 | 12/2004 | Rawnick et al. |
| 2005/0007209 A1 | 1/2005 | Brown et al. |
| 2005/0017819 A1 | 1/2005 | Brown et al. |
| 2005/0017915 A1 | 1/2005 | Brown et al. |
| 2005/0024167 A1 | 2/2005 | Rawnick et al. |

* cited by examiner

EMBEDDED MOEMS SENSOR FOR FLUID DIELECTRICS IN RF APPLICATIONS

BACKGROUND OF THE INVENTION

1. Statement of the Technical Field

The inventive arrangements relate generally to RF systems, and more particularly to embedded sensors for monitoring the state of dielectric fluid used in such systems.

2. Description of the Related Art

Glass ceramic substrates calcined at 850–1,000 C are commonly referred to as low-temperature co-fired ceramics (LTCC). This class of materials have a number of advantages that make them especially useful as substrates for RF systems. For example, low temperature 951 co-fire Green Tape™ from Dupont® is Au and Ag compatible, and it has a thermal coefficient of expansion (TCE) and relative strength that are suitable for many applications.

Recent interest in fluid dielectric materials suggest the use of LTCC as a substrate because of its known resistance to chemical attack from a wide range of fluids. The material also has superior properties of wetability and absorption as compared to other types of solid dielectric material. These factors, plus LTCC's proven suitability for manufacturing miniaturized RF circuits, make it a natural choice for use in RF devices incorporating fluid dielectrics.

Still, the use of fluid dielectrics raises new potential problems. For example, fluid dielectrics can suffer degradation from a variety of factors. The degradation can occur due to temperature variations, micro-gravity, phase separation, particulate settling and orientation, ionic migration, dendritic growth, and other intrinsic molecular separation phenomena.

Some of these problems are less likely to occur in dynamic systems. However, even in the case of dynamic systems, fluids can separate due to particle fallout, particle separation, sedimentation, eddy effects and so on. These kinds of fluid degradations will effect the overall electrical characteristics of the fluid dielectric, regardless of whether the fluid is a dielectric suspension, dielectric agglomerate, a dielectrically loaded fluid, or a polymer blend.

The refractive index of a substance is generally defined as the ratio of the velocity of electromagnetic radiation in a vacuum to its velocity in the particular substance. Using laboratory equipment, the refractive index of the substance can be determined based on the extent to which the decrease in velocity causes incident radiation to change direction as it passes from one medium to another. Laboratory measurement equipment can be used to measure this change in direction to qualitatively analyze substances for purity and also permit analysis of simple mixtures containing known components.

SUMMARY OF THE INVENTION

The invention concerns a method for monitoring the condition of a fluid dielectric in an RF system. The method can include the steps of transmitting optical radiation through a portion of the fluid dielectric contained within a dielectric substrate of said RF system; measuring at least one parameter indicative of a change of direction of the optical radiation; and determining a condition of the fluid dielectric based on the measured parameter. The method can include comparing the change in direction to an expected change of direction for the fluid dielectric in a non-degraded condition. Alternatively, or in addition thereto, the method can include the step of calculating a refractive index of the fluid dielectric. The refractive index can be compared to an expected refractive index of the fluid dielectric in a non-degraded condition. The material for the dielectric substrate can be selected to include a low temperature cofired ceramic.

The method can also include the step of selectively varying an angle of incidence of the transmitted optical radiation upon the fluid dielectric. In this way, the optical radiation can be swept through a larger volume of the fluid dielectric to ensure that the measured results do not merely represent a localized phenomena. If the angle of incidence is varied, the method can further include the step of controlling a Micro-Opto-Electro-Mechanical System (MOEMS) device or miniature electro-optical device to vary the angle of incidence. The method can also include the step of selecting the optical radiation transmitted through the fluid dielectric from the group consisting of infrared, ultraviolet, and visible light.

According to another aspect of the invention, the method can include the step of communicating a fault condition if a condition of the fluid dielectric is degraded. Alternatively, or in addition thereto, the method can include the step of modifying one or more operating parameters of the RF system if a condition of the fluid dielectric is determined to be degraded. The operating parameter that is modified can be selected to compensate for an effect to the RF system caused by the fluid dielectric that is determined to be degraded.

According to yet another aspect of the invention, the invention can include an RF system. The RF system can include one or more RF circuits coupled to a fluid dielectric. The RF circuit can be disposed on a portion of a dielectric substrate which also contains the fluid dielectric. A light source is provided for transmitting optical radiation through a portion of the fluid dielectric in a transmitted direction. The optical radiation produced by the light source can be infrared, ultraviolet, or visible light. The system also includes a sensor measuring at least one parameter indicative of a change of direction of the optical radiation relative to the transmitted direction. According to one aspect, the light source and/or the sensor can be disposed within the dielectric substrate of the RF system. An output of the sensor can be coupled to a processor for determining a condition of the fluid dielectric based on the parameter.

The processor can compare the change in direction to an expected change of direction for the fluid dielectric in a non-degraded condition. Alternatively, or in addition thereto, the processor calculates a refractive index of the fluid dielectric. This calculated refractive index value can be compare to an expected refractive index of the fluid dielectric in a non-degraded condition.

The RF system can also include a light steering device. The light steering device can be responsive to a control signal for the purpose of selectively varying an angle of incidence of the transmitted optical radiation upon the fluid dielectric. According to one aspect, the light steering device can comprise a Micro-Opto-Electro-Mechanical System (MOEMS) device which can be embedded in a dielectric substrate of the RF system.

The processor can transmits a fault notification if a condition of the fluid dielectric is determined to be degraded. Alternatively, or in addition thereto, one or more operating parameters of the RF system can be modified if a condition of the fluid dielectric is determined to be degraded. For example, the operating parameter that is modified can be selected to compensate for an effect to the RF system caused by the fluid dielectric that is determined to be degraded.

DETAILED DESCRIPTION OF THE PREFERRED EMBODIMENTS

Figure 1:
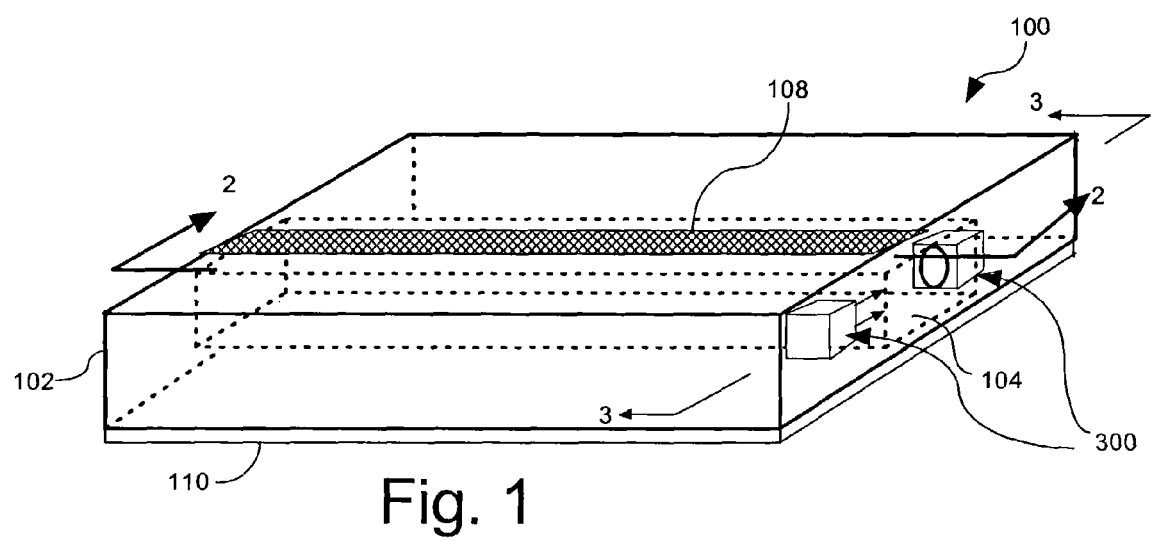
FIG. 1 is a perspective view of an RF device that is useful for understanding the present invention.
Figure 2:
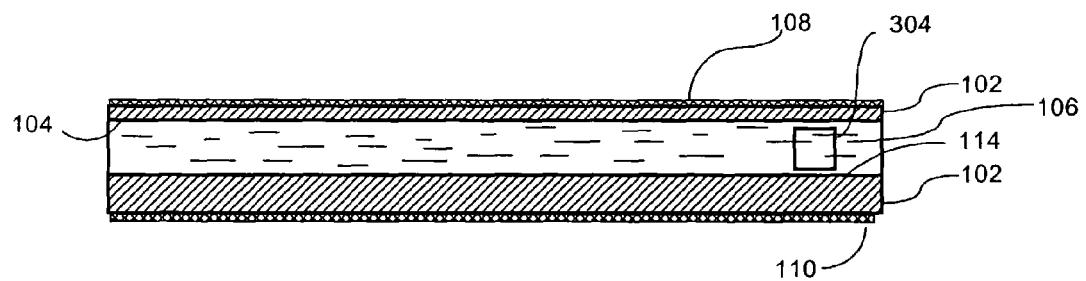
FIG. 2 is a cross-sectional view of the RF device in FIG. 1, taken along line 2—2.

An RF device formed on a dielectric substrate is illustrated in FIGS. 1 and 2. The RF device 100 can include any type of RF circuit or component that advantageously makes use of one or more types of fluid dielectric to enhance performance or aid in controlling an operating parameter of the device. In FIG. 1, the RF circuitry is illustrated as including an RF transmission line component 108. However, the invention is not so limited. For example, the RF componentry can include, without limitation, antenna elements, matching sections, delay lines, beam steering elements, tunable transmission lines, stubs and filters, variable attenuators, cavity structures, and any other type of RF component that can benefit from the use of fluid dielectrics.

The RF device 100 also includes one or more cavity structures 104 formed in dielectric substrate 102. The cavity structure 104 can be provided for constraining or transporting a fluid dielectric 106 within a defined region of the substrate 102 for advantageously utilizing the fluid dielectric 106 in the RF device. For example, the cavity structure 104 can define a fluid reservoir for storing fluid dielectric 106 when it is not in use. Alternatively, the cavity structure 104 can be a portion of a conduit used for transporting the fluid dielectric 106 from one portion of the substrate to another. Further, the cavity structure can be provided for constraining the fluid dielectric 106 in a predetermined region that is directly coupled to an RF element. For example, in FIG. 1, the cavity structure 104 is positioned generally adjacent to the transmission line 108 so that the electrical properties of the fluid dielectric can directly influence the operational characteristics of the transmission line element.

In some instances it can also be desirable to include a conductive ground plane 110 on at least one side of the substrate 102. For example, the ground plane 110 can be used in those instances where the RF circuitry includes microstrip circuit elements such as transmission line 108. The conductive ground plane 110 can also be used for shielding components from exposure to RF and for a wide variety of other purposes. The conductive metal ground plane can be formed of a conductive metal that is compatible with the substrate 102.

The substrate 102 can be formed of a ceramic material. Any of a wide variety of ceramics can be used for this purpose. However, according to a preferred embodiment, the substrate can be formed of a glass ceramic material fired at 850° C. to 1,000° C. Such materials are commonly referred to as low-temperature co-fired ceramics (LTCC).

Commercially available LTCC materials are commonly offered in thin sheets or tapes that can be stacked in multiple layers to create completed substrates. For example, low temperature 951 co-fire Green Tape™ from Dupont® may be used for this purpose. The 951 co-fire Green Tape™ is Au and Ag compatible, has acceptable mechanical properties with regard to thermal coefficient of expansion (TCE), and relative strength. It is available in thicknesses ranging from 114 $\mu$m to 254 $\mu$m. Other similar types of systems include a material known as CT2000 from W. C. Heraeus GmbH, and A6S type LTCC from Ferro Electronic Materials of Vista, Calif. Any of these materials, as well as a variety of other LTCC materials with varying electrical properties can be used.

Over time, the fluid dielectric 106 can become degraded. The degradation can occur due to temperature variations, micro-gravity, phase separation, particulate settling and orientation, ionic migration, dendritic growth, and other intrinsic molecular separation phenomena. Fluids can also separate due to particle fallout, particle separation, sedimentation, eddy effects and so on. Any of these fluid degradations can potentially affect the overall electrical characteristics of the fluid dielectric, regardless of whether the fluid is a dielectric suspension, dielectric agglomerate, a dielectrically loaded fluid, or a polymer blend. Finally, deposits can accumulate on surfaces 114 of the cavity structure 104. In order to track these effects and potentially compensate for fluid degradations, it is advantageous to monitor the condition of the fluid dielectric.

A dielectric fluid will generally have a unique refractive index that can be accurately measured. The refractive index will vary with the condition of the mixture. Accordingly, a sensor system 300 can be provided to monitor the fluid dielectric condition. The sensor system can be used to detect degradation of the fluid dielectric by measuring changes in the refractive index of the fluid dielectric. In this regard, a light source 302 and a sensor circuit 304 can be provided for detecting variations in an optical beam transmitted through the fluid dielectric 106. According to a preferred embodiment, the sensor circuit 304 can measure at least one parameter indicative of a change in the transmission direction of light transmitted by the light source 302 by detecting where the light strikes the sensor. This measured data can be used directly or, according to a preferred embodiment, can be used to calculate a refractive index of the fluid dielectric.

Figure 3:
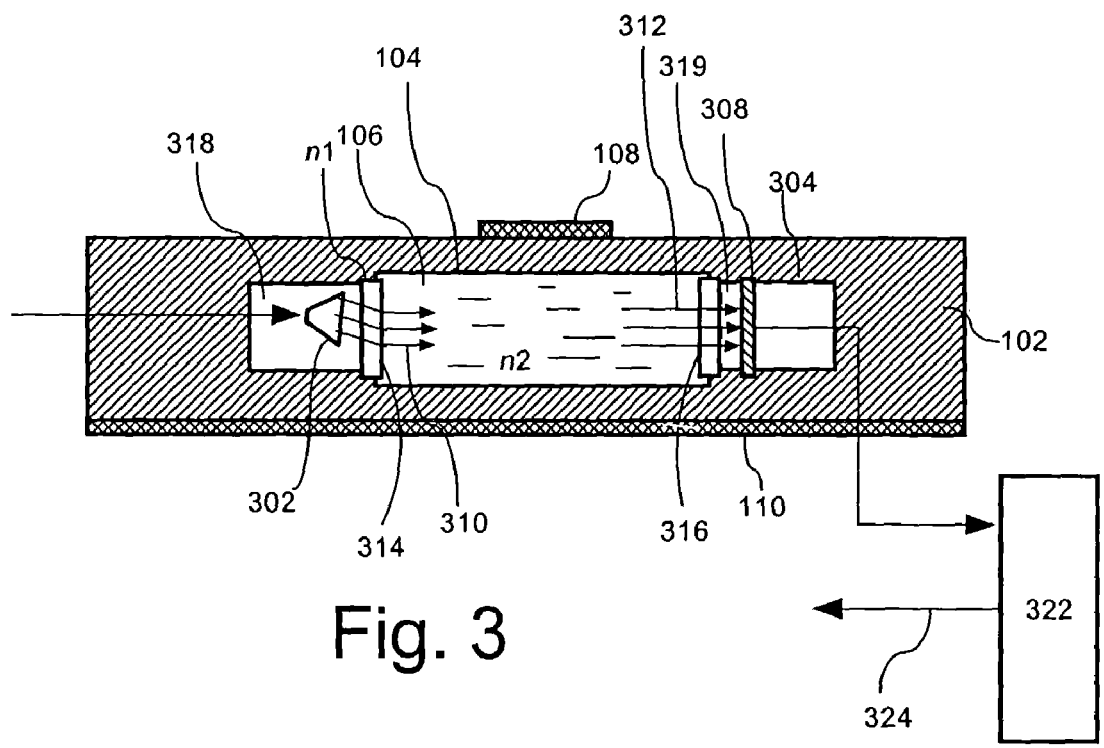
FIG. 3 is a cross-sectional view of the RF device in FIG. 1, taken along line 3—3.

Referring now to FIG. 3, a basic sensing system 300 is shown in more detail. The light source 302 and the sensor circuit 304 can be embedded within the substrate 302 on opposing sides of the cavity structure 104. According to a preferred embodiment, the light source can be a coherent light source. For example, a diode laser light source or any alternate laser light source can be used for this purpose. Further, the light source 302 can be selected to generate laser light of any wavelength suitable for substantially penetrating the dielectric fluid 106 contained in the cavity 104. The light source can be in the infrared, visible or ultraviolet ranges, without limitation. The wavelengths of photonic radiation can be selected to have a frequency in the range from between about 200 nanometers to about 4000 nm. Wavelengths of photonic radiation outside this frequency range will not be transmitted efficiently through windows of InGaAs or InP. Thus, for example, laser light in the 600 to 800 nm wavelength range can be used.

The light source 302 can be formed from any suitable device including for example diode semiconductor lasers. The light source can be integrated within the substrate 102 during or after the co-firing process. Post-cofire integration is preferred to prevent thermal degradation in the case of commercially available light source devices. If the light source is integrated within the substrate 102 during the cofiring process, it is preferably made from InGaAs or InP type semiconductor materials. However, the invention is not so limited and can be any of a wide variety of commercially available LEDs that satisfy the wavelength criteria outlined above. If an LED is used, it is preferably integrated into the device after the LTCC co-fire process to avoid degradation caused by the associated application of heat. Examples of diode laser light sources that would be suitable for this application include the following models available from Hewlett-Packard: Type HLMA-KH00, HLMP-BG11, HLMP-BD16, and HLMM-PL00.

The sensor circuit 304 is preferably designed to detect the light transmitted by the light source 302. For example, the sensor circuit can be designed to detect incident light in the 600 to 800 nm wavelength range. The sensor circuit 304 can include at least one sensing surface 308 formed of InGaAs or InP type semiconductor material. These materials provide optimum otpical transmission of coherent light over the designated wavelength range. In particular, the material composition of InGaAs and InP show excellent transmissity to photonic radiation over the frequency range 200 nm to 4000 nm. Further, InGaAs and InP are physically and chemically compatible with LTCC co-firing processes. Accordingly they can be installed before or after the co-firing process.

The sensing element used in this application can be any of a wide variety of commercially available off-the-shelf photomicrosensor (PMS). For example, PMS devices are commercially available from Omron Electronics LLC of Schaumburg, Ill. PMS devices may include amplified or non-amplified, light modulation, or miniature transmissive with 2–3 mm slot width, 2.8–3.9 mm depth and phototransistor design. Specific models from OMRON that would be suitable for the present application include Type EE-SX1103, SX1105, and SX1106. The sensor can be positioned so that light from the light source striking the sensor indicates that the fluid has a desired index of refraction. When light fails to strike the sensor, this can be an indication that the index of refraction for the fluid has changed.

A PMS sensor or sensor suite could be integrated on the LTCC substrate after the co-firing process. Notably, the LED and sensor both have to be integrated after the co-fire process, because the high fire temperature would thermally degrade the devices. The PMS sensor and LED can be attached to the LTCC subsystem with an SMT process—soldering, brazing, adhesive, etc. Sensor and laser or LED attachment does not require a hermetic bond. The fluid subsystem requires a hermetic seal to prevent leakage of fluid.

Window 314 and window 316 can be provided for facilitating the transmission of light from the lights source 302 to the fluid dielectric 106, and from the fluid dielectric to the sensor circuit 304. Preferred materials for windows 314, 316 can include InGaAs or InP. These materials are particularly well suited for the present application as they exhibit optimum transmission clarity at the wavelengths of interest. Further, because of their compatibility with the co-firing process, these materials can be installed prior to the co-firing step. Alternate materials can include GaAs or silicon, although these materials are not suitable for effective transmission of UV or infrared photonic radiation.

As illustrated in FIG. 3, light passes from the lights source 302, and into medium 318. The light then passes into window 314 having an index of refraction n1 before entering into the fluid dielectric which has an index of refraction n2. Subsequently the light passes through window 316 and medium 319 before impinging upon sensing surface 308 where it is detected by the sensor circuit 304. Mediums 318 and 319 can be inert gases or any suitable optically transparent material provided that they have an refractive index generally consistent with the material of the windows 314, 316. Material compositions that have an index of refraction different from windows 314, 316 are generally not preferred. With the foregoing arrangement, the sensor system 300 can be used as a refractometer to measure the refractive index of the fluid dielectric.

In order to accurately detect the shift in refractive index measurements, both the transmission and receiving windows 314, 316 are preferably of the same material composition. Using the same material composition will reduce photonic transmission and receiving irregularities, ambiguities, optical aberrations, and optical loss. All of these characteristics can result in inaccurate refractive index measurements. The InGaAs and InP window materials may be integrated into the light source sensor or exist free standing and independent from the light source.

The index of refraction of a material is the ratio of the speed of light in vacuum to the speed of light in that material. The index of refraction n can be expresses as $n=c/v$ where c is the speed of light in a vacuum and v is the speed of light in the material. The index of refraction can also be expressed as $n=\lambda_0/\lambda$ where $\lambda_0$ is the wavelength of the light in the vacuum and $\lambda$ is the wavelength of the light in the medium.

Figure 3A:
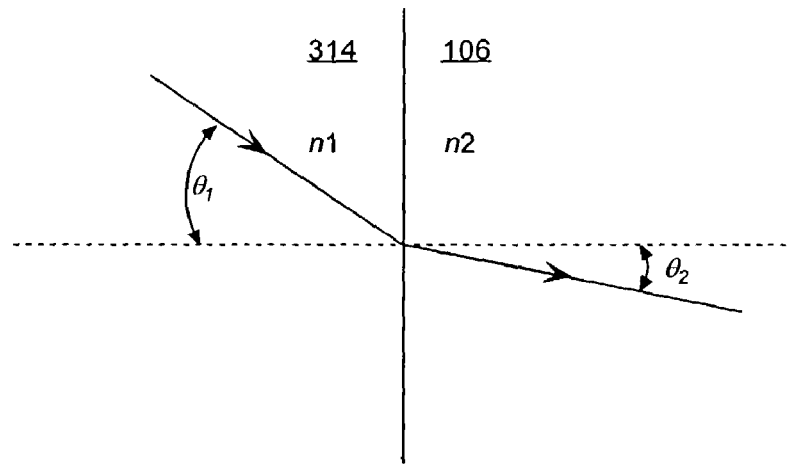
FIG. 3A is an optical diagram that is useful for understanding the optics in FIG. 3.

Referring to FIG. 3A, light from light source 302 is transmitted in a first direction though window 314 so as to form an incident angle $\theta_1$. When the light transitions from the material of the window 314 into the fluid dielectric 106, it will be refracted provided that the refractive index of the window 314 and the fluid dielectric 106 are different from one another. More particularly, the light experiences a change in direction so that the departure angle $\theta_2$ of the light ray as it passes into the fluid dielectric will vary from that of the incident angle $\theta_1$. If the incident angle $\theta_1$ is the angle of the incident light ray relative to the normal to the surface medium 1, and $\theta_2$ is the angle relative to the normal in medium 2, then:

$$\sin \theta_1/\sin \theta_2 = \lambda_1/\lambda_2 = n_1/n_2$$

where $\lambda_1$ and $\lambda_2$ are respectively the wavelengths in medium 1 and medium 2. Similarly, $n_1$ and $n_2$ are the respective index of refraction in medium 1 and medium 2. Accordingly, if index of refraction $n_1$ in the first medium (window 314) is known, and the angles $\theta_1$ and $\theta_2$ are known or can be calculated based on available information, then the index of refraction $n_2$ of the second material (fluid dielectric 106) can be calculated.

At least one parameter can be measured by sensor 304 that is indicative of the change in direction that the light beam experiences. This can be accomplished by using information regarding the geometry of the system, e.g. incident angle $\theta_1$, the location of the interface between window 314 and fluid dielectric 106 relative to the sensing surface 308. In particular, by using the foregoing information and measuring at least one parameter, such as a detected location where the light beam strikes the sensing surface 308, then the index of refraction $n_2$ for the fluid dielectric 106 can be calculated.

Still, it will occur to those skilled in the art that it is not necessary to actually calculate the index of refraction for the fluid dielectric 106. Instead, a look up table can be used to determine acceptable locations where the light beam should strike the sensing surface 308 given information regarding the transmitted beam. Similarly, if the light beam strikes the sensing surface 308 outside a predetermined range, then this is a measured parameter that can be an indication of degraded fluid dielectric 106. However, the invention is not limited in this regard, and any other measured parameter can also be used to detect a change in direction experienced by the light beam.

In a basic embodiment shown in FIG. 3, the angle of incidence of the light beam on a surface of the fluid dielectric 106 can be selected so that the beam of light, after being diffracted by transitioning into the fluid dielectric, will travel in a direction that is substantially perpendicular to the plane defined by window 314. Consequently, the light beam will generally traverse a central volume of the fluid dielectric 106 located between windows 3114 and 316. The precise location on the sensing surface 308 struck by the light beam is a parameter that can be monitored by controller 322. Controller 322 can be comprised of a programmable microprocessor, general purpose computer programmed with a set of instructions or any other electronic circuitry suitable for performing the functions as described herein.

A predetermined location or area on sensing surface 308 can be defined in which the light beam should strike the sensing surface 308 if the fluid dielectric has an index of refraction anticipated for the particular fluid when it is not degraded. If the position of the light beam is determined by controller 322 as having departed from the predetermined location or area, the controller 322 can communicate a fault condition. According to an alternative embodiment, the controller 322 can also calculate an index of refraction or some other value relevant useful for analyzing the condition of the fluid dielectric 106.

Alternatively, or in addition to communicating a fault condition, the controller 322 can modify one or more parameters relating to the operation of the RF device so as to at least partially compensate for the variation in the electrical properties of the fluid dielectric 106. For example, the measured refractive index of the fluid dielectric 106 (as determined by controller 322) can indicate that the fluid dielectric has degraded in such a way as to change an electrical characteristic of the fluid dielectric 106. In that case a control program of controller 322 or selected operating parameters can be modified so that RF device 100 continues to respond properly despite the fluid dielectric degradation. For example, one or more operating parameters of the RF device 100 can be controlled by controller 322 via a control signal 324. Alternatively, or in addition thereto, a change in the fluid dielectric may require a change in the volume, position or composition of the fluid dielectric to compensate for the degraded fluid. These functions can also be controlled by controller 322.

According to an alternative embodiment of the invention, the sensor system 300 can be somewhat more complex. For example, instead of a simple fixed beam light source, the light source can be provided in a steered arrangement. This produces a higher order of functionality and produces a wider dynamic range. In particular, the steered approach has the advantage of allowing the beam to be scanned through the fluid dielectric over a larger volume so that the measurement of the refractive index for the fluid dielectric does not occur exclusively at one location. This scanning feature can be important as degradation to the fluid dielectric will not necessarily occur in a uniform way within the fluid volume. For example, fluid closer to the walls of the cavity structure can exhibit differing degrees or types of degradation as compared to the fluid dielectric at a center of the volume. The scanable beam can also be useful for detecting sediments, deposits and film glaze that may accumulate at or near the walls and surfaces that define the cavity structure.

Any suitable arrangement can be used for scanning the beam produced by the light source. However, according to a preferred embodiment, an electronically controlled MicroOptoElectroMechanical Systems (MOEMS) array can be used to steer the light beam through the fluid dielectric. For example, the MOEMS array could be a micro-mirror array. Such devices are comprised of a planar array of microscopically small mirrors that can be selectively tilted in response to a control signal. Tilting the mirror allows a transmitted direction of a light beam to be selectively varied. MOEMS arrays are available from a wide variety of commercial sources. For example, Digital Micromirror Devices (DMD) are commercially available from Texas Instruments of Plano, Tex. These devices are semiconductor-based "light switch" arrays that can include thousands of individually addressable, tiltable, mirror-pixels. It will be appreciated that, for the purposes of the present invention, such large arrays are not required. For example, a 10×10 lenslet micro-mirror array can be sufficient, for steering a light beam as described herein. Still, the invention is not limited to any one configuration of an MOEMS device or any number of lenslets. Any of a wide variety of such devices in different array sizes can be used provided that they are capable of steering a light beam. For example, the MOEMS lenslets can be in a configuration of 1×1, 2×2, 3×3, 4×4, 40×40 and so on, without limitation. The number of lenslets required is primarily dependent on the area of the light beam and physical size limits imposed by the device.

Figure 4:
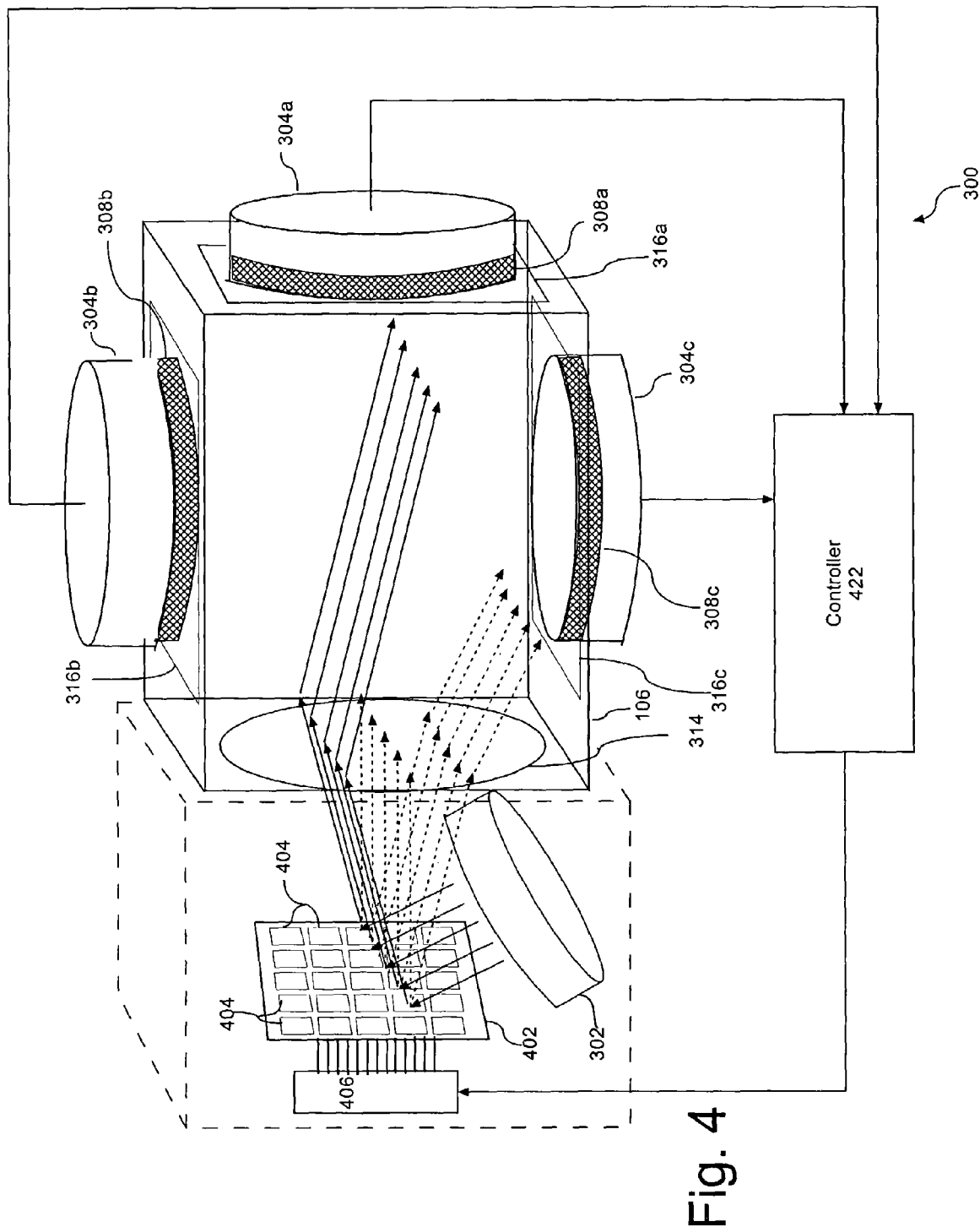
FIG. 4 is a drawing that is useful for understanding a scanned beam embodiment of the invention.

A steerable light beam arrangement is illustrated in FIG. 4, where reference numerals common to FIG. 3 are used to identify common structure. In FIG. 4, windows 314, 316a, 316b, 316c can provide an optical access to the fluid dielectric 106 that is contained in the dielectric substrate 102 (not shown). The light source 302 again can be a diode laser light source. Similarly, one or more sensor circuits 304a, 304b, 304c can include a semiconductor sensing surface 308a, 308b, 308c formed of a suitable material such as InGaAs or InP type semiconductor material.

Significantly, the light source 302 in this embodiment also includes a light steering device 402 for selectively varying a direction of the laser light produced by the diode laser light source 306. For example a MOEMS device can be used for this purpose. According to one embodiment, the MOEMS device can consist of a micro-mirror array of one or more mirrors and an associated array driver circuit 404. In that case, the array driver circuit is responsive to signals from controller 422 for varying an angular orientation of a plurality of hinged micro-mirrors 406. Controller 422 can be comprised of a programmable microprocessor, general purpose computer or any other electronic circuitry suitable for performing the functions as described herein. The micro-mirrors can selectively redirect a beam of light from diode laser light source 306 to scan the beam through a volume of fluid dielectric so that a transmitted beam can be directed after refraction, toward one or more sensing surfaces 308a, 308b, 308c. The respective sensor circuit 304a, 304b, 304c can detect the incidence of the scanned beam at a location on the sensing surface 308.

As illustrated in FIG. 4, controller 422 can scan the transmitted light beam through a range of incident angles through the fluid dielectric 106. The selected angle at any given moment will be determined based on control signals communicated to the array driver circuit 404. Accordingly, controller 422 can have information regarding the incident beam angle. Using this information concerning the angle of the transmitted beam, and information communicated from sensing circuits 304a, 304b, or 304c indicating that a scanned beam is striking (or is not striking) one of the sensing surfaces 308a, 308b, 308c, an index of refraction evaluation can be performed for a series of spatially separated optical paths through the fluid dielectric 106.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

I claim:

1. A method for monitoring the condition of a fluid dielectric in an RF system comprising the steps of:
    transmitting optical radiation through a portion of said fluid dielectric contained within a dielectric substrate of said RF system;
    measuring at least one parameter indicative of a change of transmission direction of said optical radiation caused by said fluid dielectric.

2. The method according to claim 1 further comprising the step of selecting a material for said dielectric substrate to be a low temperature cofired ceramic.

3. The method according to claim 1 further comprising the step of comparing said change in direction to an expected change of direction for said fluid dielectric in a non-degraded condition.

4. The method according to claim 1 further comprising the step of calculating a refractive index of said fluid dielectric.

5. The method according to claim 3 further comprising the step of comparing said refractive index to an expected refractive index of said fluid dielectric in a non-degraded condition.

6. The method according to claim 1 further comprising the step of dynamically varying an angle of incidence of said transmitted optical radiation upon said fluid dielectric.

7. The method according to claim 6 further comprising the step of controlling a Micro-Opto-Electro-Mechanical System (MOEMS) to vary said angle of incidence.

8. The method according to claim 1 further comprising the step of selecting said optical radiation from the group consisting of infrared, ultraviolet, and visible light.

9. The method according to claim 1 further comprising the step of communicating a fault notification if a condition of said fluid dielectric is degraded.

10. The method according to claim 1 further comprising the step of determining a condition of said fluid dielectric based on said parameter.

11. The method according to claim 1 further comprising the step of modifying at least one operating parameter of said RF system if a condition of said fluid dielectric is determined to be degraded.

12. The method according to claim 11 wherein said at least one operating parameter that is modified is selected to compensate for an effect to said RF system caused by said fluid dielectric that is determined to be degraded.

13. An RF system comprising:
    an RF circuit disposed on a dielectric substrate;
    a fluid dielectric contained within said dielectric substrate;
    a light source transmitting optical radiation through a portion of said fluid dielectric; and
    a sensor measuring at least one parameter indicative of a change of transmission direction of said optical radiation caused by said fluid dielectric.

14. The RF system according to claim 13 wherein at least one of said light source and said sensor is embedded within said dielectric substrate.

15. The RF system according to claim 13 wherein said substrate is a low temperature cofired ceramic.

16. The RF system according to claim 13 wherein said processor compares said change of direction to an expected change of direction for said fluid dielectric in a non-degraded condition.

17. The RF system according to claim 13 wherein said processor calculates a refractive index of said fluid dielectric.

18. The RF system according to claim 17 wherein said processor compares said refractive index to an expected refractive index of said fluid dielectric in a non-degraded condition.

19. The RF system according to claim 13 further comprising a light steering device responsive to a control signal, said light steering device selectively varying an angle of incidence of said transmitted optical radiation upon said fluid dielectric.

20. The RF system according to claim 19 wherein said light steering device comprises a Micro-Opto-Electro-Mechanical System (MOEMS) device.

21. The RF system according to claim 20 wherein said MOEMS device is embedded in a dielectric substrate of said RF system.

22. The RF system according to claim 13 wherein said optical radiation produced by said light source is selected from the group consisting of infrared, ultraviolet, and visible light.

23. The RF system according to claim 13 wherein said processor transmits a fault notification if a condition of said fluid dielectric is degraded.

24. The RF system according to claim 13 wherein at least one operating parameter of said RF system is modified if a condition of said fluid dielectric is determined to be degraded.

25. The RF system according to claim 24 wherein said at least one operating parameter that is modified is selected to compensate for an effect to said RF system caused by said fluid dielectric that is determined to be degraded.

26. The RF system according to claim 13 further comprising a processor responsive to an output of said sensor, said processor determining a condition of said fluid dielectric based on said parameter.

27. The RF system according to claim 26 wherein said condition affects at least one electrical characteristic of said fluid dielectric.

28. The RF system according to claim 26 wherein said electrical characteristic is at least one of a permittivity and a permeability.

* * * * *